(12) United States Patent
Kraemer et al.

(10) Patent No.: US 10,541,062 B2
(45) Date of Patent: Jan. 21, 2020

(54) APPARATUS FOR MOVABLY SUSPENDING AN X-RAY GRID, ARRANGEMENT WITH AN X-RAY GRID AND METHOD FOR OPERATING AN X-RAY GRID

(71) Applicant: SIEMENS HEALTHCARE GMBH, Erlangen (DE)

(72) Inventors: Alexander Kraemer, Irchenrieth (DE); Josef Zeidler, Marktredwitz (DE)

(73) Assignee: Siemens Healthcare GmbH, Erlangen (DE)

( * ) Notice: Subject to any disclaimer, the term of this patent is extended or adjusted under 35 U.S.C. 154(b) by 310 days.

(21) Appl. No.: 15/622,338

(22) Filed: Jun. 14, 2017

(65) Prior Publication Data

US 2017/0358378 A1    Dec. 14, 2017

(30) Foreign Application Priority Data

Jun. 14, 2016    (DE) .................. 10 2016 210 527

(51) Int. Cl.

| | |
|---|---|
| *A47B 81/00* | (2006.01) |
| *A61B 6/02* | (2006.01) |
| *G21K 1/02* | (2006.01) |
| *A61B 6/00* | (2006.01) |
| *G21K 1/06* | (2006.01) |

(52) U.S. Cl.
CPC ............ *G21K 1/025* (2013.01); *A61B 6/4291* (2013.01); *A61B 6/484* (2013.01); *G21K 1/06* (2013.01); *G21K 2207/005* (2013.01)

(58) Field of Classification Search
CPC ...... A61B 6/583; A61B 6/0457; A61B 6/4291
See application file for complete search history.

(56) References Cited

U.S. PATENT DOCUMENTS

| | | | |
|---|---|---|---|
| 5,373,546 A | 12/1994 | Holzermer | |
| 9,901,315 B2 * | 2/2018 | Farbizio | ................ A61B 6/025 |
| 2006/0182226 A1 | 8/2006 | Yuan et al. | |

(Continued)

FOREIGN PATENT DOCUMENTS

| | | |
|---|---|---|
| CN | 103188996 A | 7/2013 |
| CN | 103629226 A | 3/2014 |

(Continued)

OTHER PUBLICATIONS

Hong, G. et al., "Computer-Controlled Micropositioning Stage with Submicrometre Accuracy", Jun. 1988, 71994-2016 China Academic Journal Electronic Publishing House, enki.net; 1988—English abstract.

*Primary Examiner* — Don K Wong
(74) *Attorney, Agent, or Firm* — Laurence Greenberg; Werner Stemer; Ralph Locher

(57) ABSTRACT

An apparatus for movably suspending an x-ray grid. The apparatus has a carrier module, in or on which the x-ray grid is arranged, and a linkage. The linkage is configured to rotate the carrier module about an axis which is vertical to the x-ray grid and/or to translate the carrier module in the plane of the x-ray grid. An x-ray arrangement has an x-ray emitter, an x-ray detector and one or more apparatus for suspending the x-ray grid between the emitter and detector. The apparatus provides for play-free kinematics which is more cost-effective than the use of known precision drives.

17 Claims, 4 Drawing Sheets

(56) References Cited

U.S. PATENT DOCUMENTS

| | | | |
|---|---|---|---|
| 2009/0066204 A1* | 3/2009 | Reina | A61B 6/06 312/223.1 |
| 2013/0235973 A1 | 9/2013 | Murakoshi et al. | |
| 2016/0035450 A1 | 2/2016 | Date et al. | |
| 2017/0299838 A1 | 10/2017 | Yi et al. | |
| 2017/0358379 A1 | 12/2017 | Kraemer et al. | |

FOREIGN PATENT DOCUMENTS

| | | |
|---|---|---|
| CN | 105228551 A | 1/2016 |
| CN | 205286379 A | 6/2016 |
| DE | 4229319 A1 | 3/1994 |
| DE | 10016038 A1 | 10/2001 |
| JP | 2010014418 A | 1/2010 |
| JP | 2010190777 A | 9/2010 |
| WO | 2008102654 A1 | 8/2008 |

\* cited by examiner

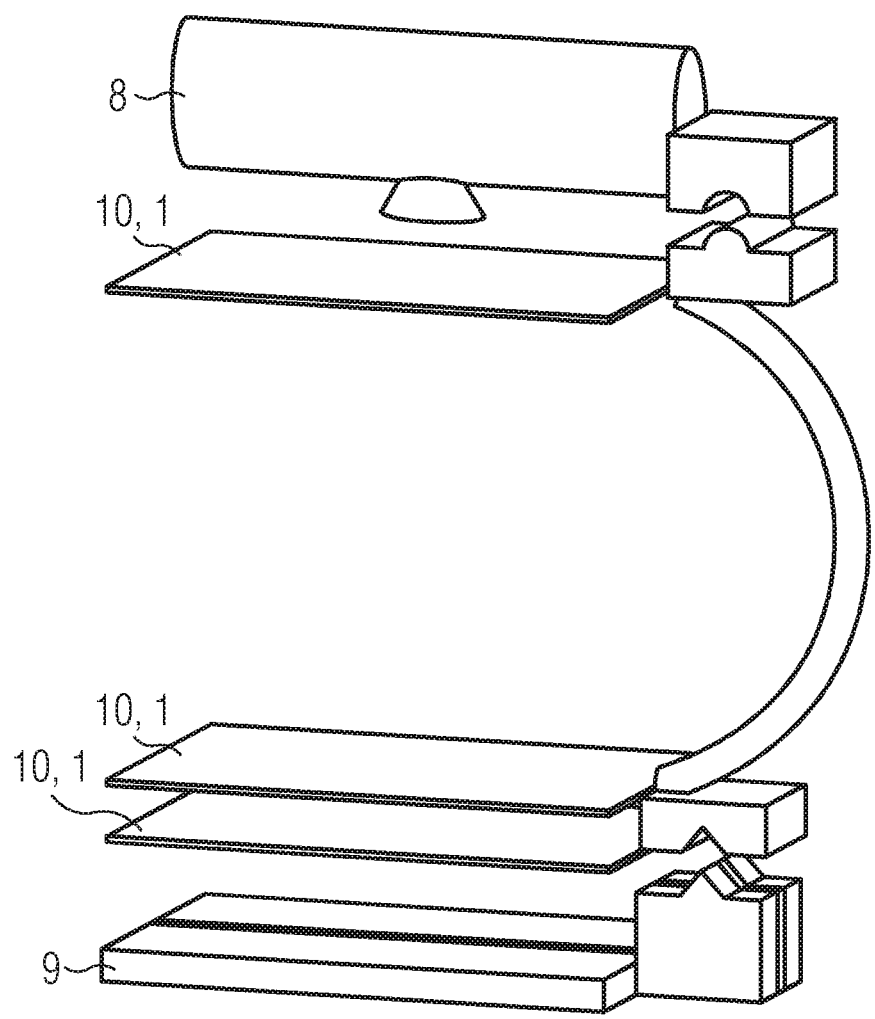

APPARATUS FOR MOVABLY SUSPENDING AN X-RAY GRID, ARRANGEMENT WITH AN X-RAY GRID AND METHOD FOR OPERATING AN X-RAY GRID

CROSS-REFERENCE TO RELATED APPLICATION

This application claims the priority, under 35 U.S.C. § 119, of German patent application DE 10 2016 210 527.2, filed Jun. 14, 2016; the prior application is herewith incorporated by reference in its entirety.

BACKGROUND OF THE INVENTION

Field of the Invention

The invention relates to an apparatus for movably suspending an x-ray grid, an arrangement with an apparatus of this type and a method for operating an arrangement of this type.

Interference grids are introduced into the radiation path between an x-ray emitter and an x-ray detector for interferometric imaging (phase contrast imaging). The interference grids must be aligned exactly with one another and with the x-ray detector and moved partly in a translational manner for the generation of the phase contrast image.

A rotation of the interference grids about small paths about the central beam axis is required inter alia for the precise alignment. A translational movement in the range of a few micrometers and with increments in the sub micrometer range is required for the scanning of the interference pattern (="phase stepping"). The accuracy requirements also require play-free hinges.

ABSTRACT OF THE INVENTION

It is accordingly an object of the invention to provide an apparatus which overcomes the above-mentioned and other disadvantages of the heretofore-known devices and methods of this general type and which provides for an apparatus and an arrangement for movably suspending an x-ray grid and a method for operating an x-ray grid, which permit a play-free rotational movement of the suspension with very good accuracy (less than one arc second) and a translational movement in the micrometer range.

With the foregoing and other objects in view there is provided, in accordance with the invention, an apparatus for movably suspending an x-ray grid. The apparatus comprises:

a carrier module carrying the x-ray grid thereon or therein; and a linkage connected to the carrier module, the linkage is configured to rotate the carrier module about an axis that extends vertically to the x-ray grid and/or to translate (i.e., move in translation) the carrier module in a plane of the x-ray grid.

In other words, in accordance with the invention the apparatus has of a carrier module which is moved by a linkage. Linkages consist of at least four links (rods, limbs) and hinges connecting them, with which they form a four-bar kinematic chain. They are available in most cases as flat transmissions, wherein the rotational axes of the four hinges are parallel to one another.

The swivel joints of the linkage are preferably embodied as plastic hinges. In plastic theory, a plastic hinge refers to a hinge which is embodied by the bearing structure if the yield strength is exceeded. It is therefore not a real hinge as an independent component, but instead a point on a construction or a bearing structure which is placed under stress as a hinge, which as far as possible is characterized by a large mechanical deformability. The prerequisite for this is generally the use of a ductile material which allows for significant plastic deformations without completely collapsing.

The invention is advantageous in that play-free kinematics is available which is more cost-effective than the use of known precision drives.

In accordance with an added feature of the invention, the linkage is trapezoid-shaped. As a result, a rotational movement of the x-ray grid is possible.

In accordance with an additional feature of the invention, the linkage can be embodied in the manner of a parallelogram. As a result, a translational movement of the x-ray grid is possible.

In accordance with another feature of the invention, the apparatus has:

four swivel joints, which connect four limbs of the linkage, wherein the swivel joints are embodied as hinge-type flexible elements.

In accordance with a further feature of the invention, the flexible elements are plastic hinges or spring hinges. As a result, a play-free movement of the x-ray grid is ensured.

In accordance with again an added feature of the invention, the linkage is formed in one piece and from sheet metal.

In accordance with again an additional feature of the invention, the apparatus has a motor-driven linear drive with a spindle, which is arranged in a diagonal of the linkage and moves the carrier module by changing the length of the diagonal.

In accordance with again a further feature of the invention, the apparatus has an electromagnet which moves the linkage. Using an electromagnet as a drive saves on costs and simplifies drive electronics.

With the above and other objects in view there is also provided, in accordance with the invention, an arrangement with an x-ray emitter and an x-ray detector, and at least one above-summarized apparatus disposed between the x-ray emitter and the x-ray detector.

In accordance with a concomitant feature of the invention, there is provided a method for operating an x-ray grid with an inventive arrangement, wherein the x-ray grid is rotated about a predeterminable angle and/or is moved translationally about a predeterminable path.

Other features which are considered as characteristic for the invention are set forth in the appended claims.

Although the invention is illustrated and described herein as embodied in a apparatus for movably suspending an x-ray grid, arrangement with an x-ray grid and method for operating an x-ray grid, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 7 shows an arrangement with a number of x-ray grids.

DETAILED DESCRIPTION OF AN EXEMPLARY EMBODIMENT

Figure 1:
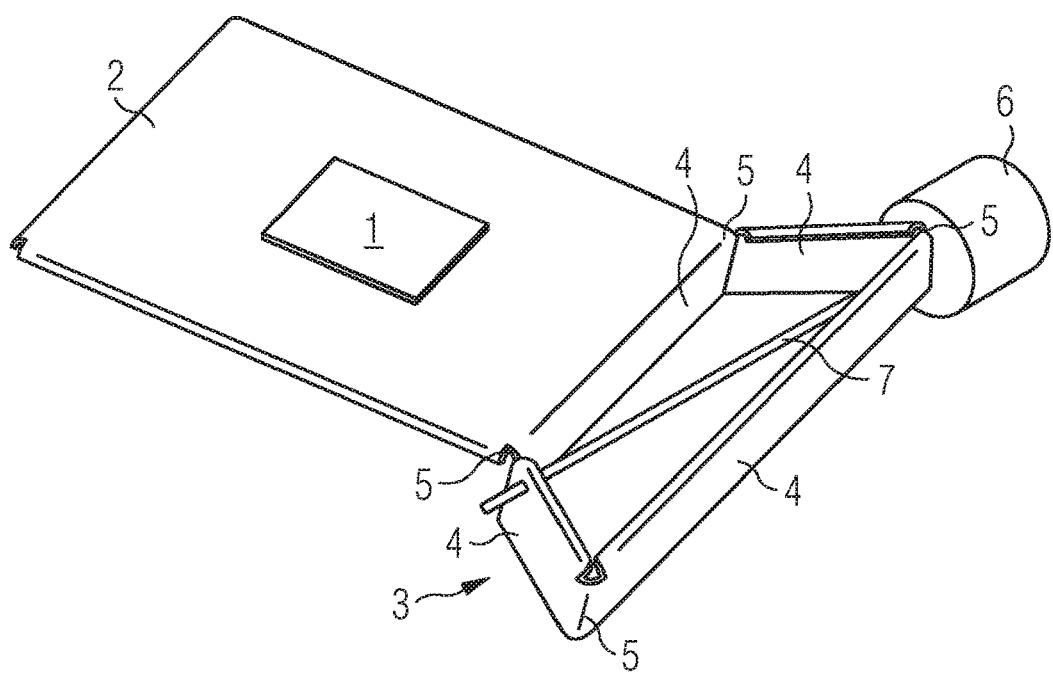
FIG. 1 is a perspective view of an apparatus for movable suspension with a trapezoid-shaped linkage.

Referring now to the figures of the drawing in detail and first, particularly, to FIG. 1 thereof, there is shown an apparatus for movably suspending an x-ray grid 1. The x-ray grid 1 is attached to a carrier module 2. The carrier module 2 can be rotated, or pivoted, by a linkage 3 about an axis at right angles to the x-ray grid 1. To this end, the linkage 3 is trapezoid-shaped. It has two parallel limbs 4 and two limbs 4 connecting the same. The limbs 4 are rotatably connected with one another using four swivel joints 5. The swivel joints 5 are embodied as plastic hinges.

The movement of the linkage 3 and thus the rotation of the carrier module 2 is carried out with the aid of a linear drive 6, the spindle 7 of which runs along the diagonal of the trapezoid. The carrier module 2 is rotated by changing the length of the diagonal (=spindle length within the linkage 3).

The carrier module 2 and the linkage 3 can preferably be formed in one piece from sheet metal. Instead of the linear drive 6, an electromagnet which moves the linkage 3 can also be used.

Figure 2:
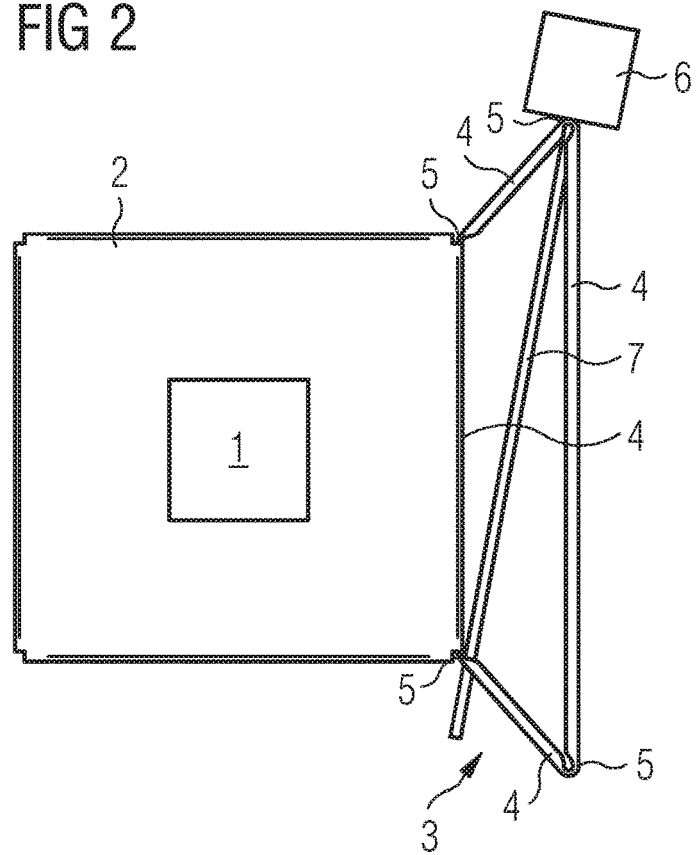
FIG. 2 shows a movable suspension with a trapezoid-shaped linkage in a first position.
Figure 3:
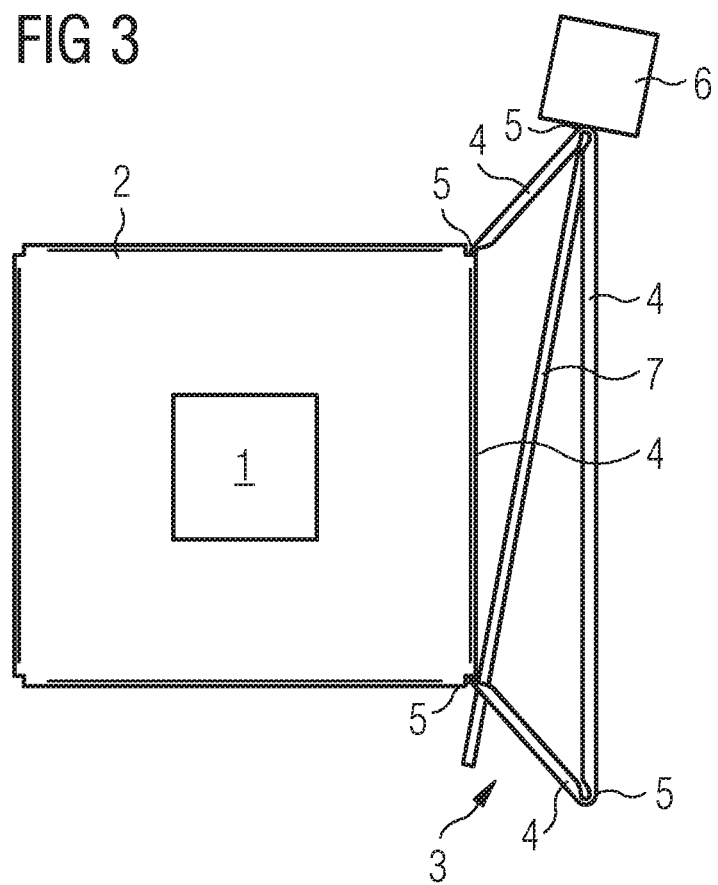
FIG. 3 shows a movable suspension with a trapezoid-shaped linkage in a second position.

FIG. 2 and FIG. 3 show the apparatus according to FIG. 1 in a top view in a first and in a second position. In the first position according to FIG. 2 the length of the spindle 7 along the diagonal of the linkage 3 is greater compared with the second position according to FIG. 3. The carrier module 2 is "tilted" about an axis which projects from the image plane.

Figure 4:
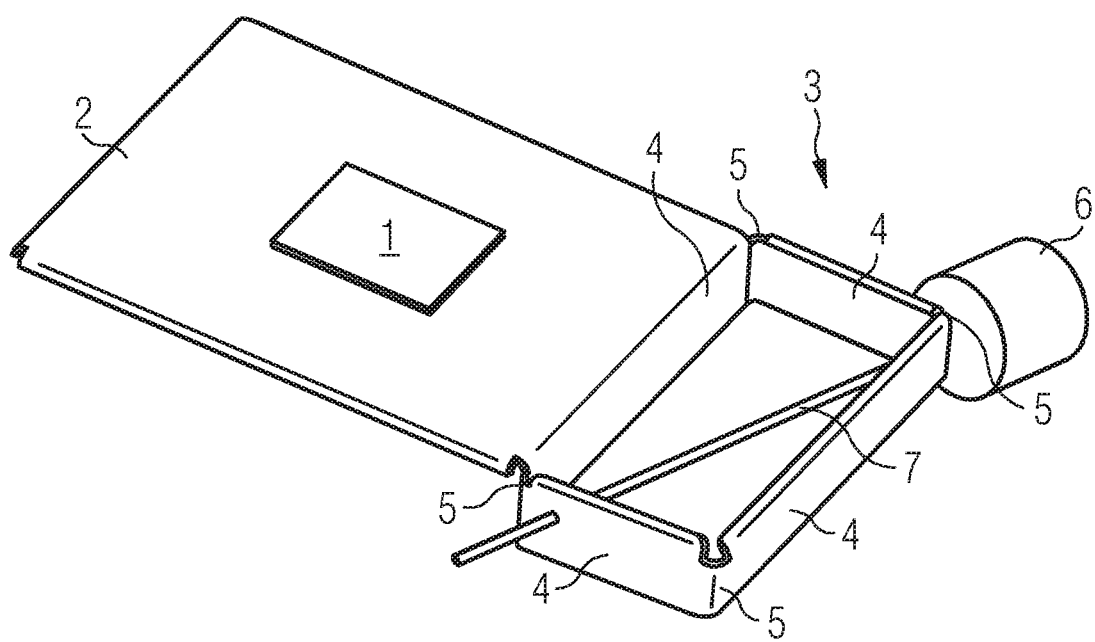
FIG. 4 shows an apparatus for movable suspension with a parallelogram-type linkage.

FIG. 4 shows an apparatus for movably suspending an x-ray grid 1. The x-ray grid 1 is attached to a carrier module 2. The carrier module 2 can be moved translationally in the plane of the x-ray grid by a linkage 3. To this end, the linkage is designed in the manner of a parallelogram. It has in each case two parallel limbs 4, which are rotatably connected to four swivel joints 5 in the corners. The swivel joints 5 are embodied as plastic hinges.

The movement of the linkage 3 and thus the translation of the carrier module 2 is carried out with the aid of a linear drive 6, the spindle 7 of which runs along the diagonal of the parallelogram. The carrier module 2 is moved by changing the length of the diagonal (=spindle length within the linkage 3).

The carrier module 2 and the linkage 3 can preferably be formed in one piece from sheet metal.

Figure 5:
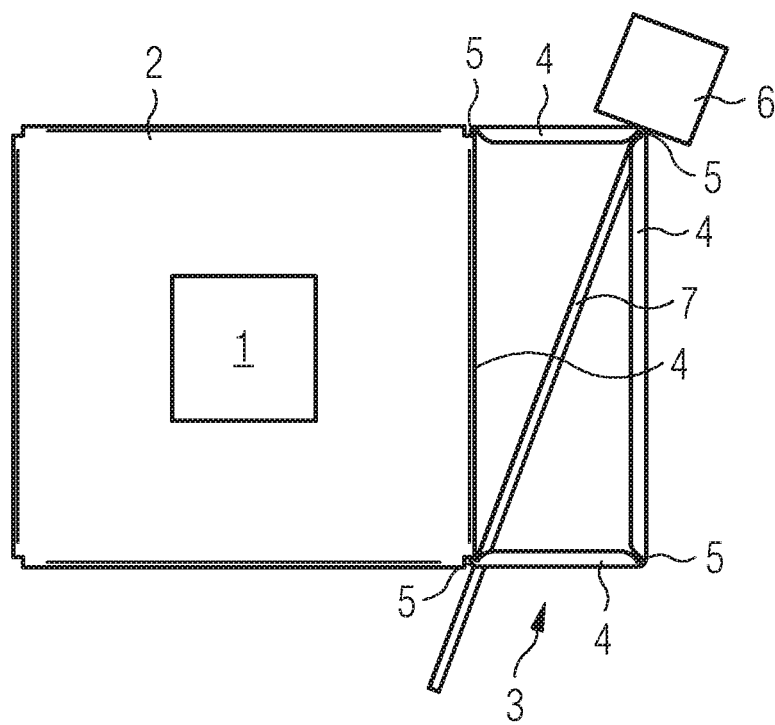
FIG. 5 shows a movable suspension with a parallelogram-type linkage in a first position.
Figure 6:
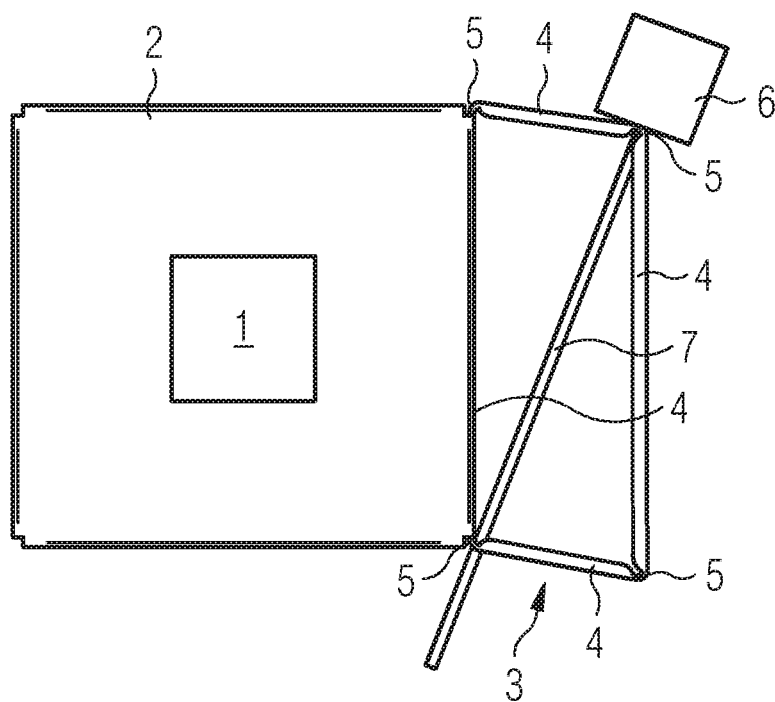
FIG. 6 shows a movable suspension with a parallelogram-type linkage in a second position.

FIG. 5 and FIG. 6 show the apparatus according to FIG. 4 in a top view in a first and in a second position. In the first position according to FIG. 5 the length of the spindle 7 along the diagonal of the linkage 3 is greater compared with the second position according to FIG. 6. In FIG. 6, the carrier module 2 is deflected compared with the first position (moved horizontally in two directions).

A number of linkages 3 can engage with the carrier module 2 so that further movements are possible.

FIG. 7 shows an interferometric arrangement for phase contrast imaging with three phase grids 1 in a grid suspension 10 in each case, which can be embodied in accordance with the apparatus from FIG. 1 and FIG. 6. The grid suspensions 10 are arranged between an x-ray emitter 13 and an x-ray detector 14.

Although the invention is illustrated and described in more detail by the exemplary embodiments, the invention is not restricted by the disclosed examples and other variations can be derived therefrom by the person skilled in the art without departing from the protective scope of the invention.

The following is a summary list of reference numerals and the corresponding structure used in the above description of the invention:

1 x-ray grid
2 carrier module
3 linkage
4 limb
5 swivel joint
6 linear drive
7 spindle
8 x-ray emitter
9 x-ray detector
10 grid suspension

The invention claimed is:

1. An apparatus for movably suspending an x-ray grid, the apparatus comprising:
   a carrier module carrying the x-ray grid thereon or therein; and
   a linkage having a shape selected from the group consisting of trapezoid and parallelogram; and
   said linkage being configured to effect at least one of the following:
      rotate said carrier module about an axis extending vertically to the x-ray grid; or
      move said carrier module in translation in a plane of the x-ray grid.

2. The apparatus according to claim 1, wherein said linkage includes four limbs and wherein:
   four swivel joints connect said four limbs of said linkage; and
   said swivel joints are flexible hinge elements.

3. The apparatus according to claim 2, wherein said flexible hinge elements are plastic hinges or spring hinges.

4. The apparatus according to claim 1, wherein said linkage is formed in one piece and from sheet metal.

5. The apparatus according to claim 1, which further comprises a motor-driven linear drive with a spindle disposed along a diagonal of said linkage, said spindle being configured to move said carrier module by changing a length of the diagonal.

6. The apparatus according to claim 1, which further comprises an electromagnet disposed and configured to move said linkage.

7. An x-ray arrangement, comprising
   an x-ray emitter and an x-ray detector; and
   at least one apparatus according to claim 1 disposed between said x-ray emitter and said x-ray detector.

8. A method of operating an x-ray arrangement, the method comprising:
   providing an x-ray arrangement according to claim 7; and
   selectively rotating the x-ray grid about a predetermined angle and/or moving the x-ray grid translationally about a predetermined path.

9. An apparatus for movably suspending an x-ray grid, the apparatus comprising:
- a carrier module carrying the x-ray grid thereon or therein;
- a linkage;
- a motor-driven linear drive with a spindle disposed along a diagonal of said linkage, said spindle being configured to move said carrier module by changing a length of the diagonal; and
- said linkage configured to effect at least one of the following:
- rotate said carrier module about an axis extending vertically to the x-ray grid; or
- move said carrier module in translation in a plane of the x-ray grid.

10. The apparatus according to claim 9, wherein said linkage is trapezoid-shaped.

11. The apparatus according to claim 9, wherein said linkage is embodied as a parallelogram.

12. The apparatus according to claim 9, wherein said linkage includes four limbs and wherein:
- four swivel joints connect said four limbs of said linkage; and
- said swivel joints are flexible hinge elements.

13. The apparatus according to claim 12, wherein said flexible hinge elements are plastic hinges or spring hinges.

14. The apparatus according to claim 9, wherein said linkage is formed in one piece and from sheet metal.

15. The apparatus according to claim 9, which further comprises an electromagnet disposed and configured to move said linkage.

16. An x-ray arrangement, comprising
- an x-ray emitter and an x-ray detector; and
- at least one apparatus according to claim 9 disposed between said x-ray emitter and said x-ray detector.

17. A method of operating an x-ray arrangement, the method comprising:
- providing an x-ray arrangement according to claim 16; and
- selectively rotating the x-ray grid about a predetermined angle and/or moving the x-ray grid translationally about a predetermined path.

* * * * *